(12) United States Patent
Read

(10) Patent No.: US 7,897,403 B2
(45) Date of Patent: *Mar. 1, 2011

(54) HYDROGEN PEROXIDE AND PERACETIC ACID INDICATORS AND METHODS

(75) Inventor: David M. Read, White Bear Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/693,553

(22) Filed: Jan. 26, 2010

(65) Prior Publication Data

US 2010/0124784 A1   May 20, 2010

Related U.S. Application Data

(60) Continuation of application No. 11/655,022, filed on Jan. 18, 2007, now Pat. No. 7,670,552, which is a division of application No. 10/037,435, filed on Dec. 31, 2001, now Pat. No. 7,192,554.

(51) Int. Cl.
   *A61L 2/00* (2006.01)
(52) U.S. Cl. .................. 436/135; 436/166; 422/83; 422/123
(58) Field of Classification Search .............. 436/135, 436/166; 422/83, 123
   See application file for complete search history.

(56) References Cited

U.S. PATENT DOCUMENTS

| | | | |
|---|---|---|---|
| 4,046,577 A | 9/1977 | Muzyczko et al. |
| 4,155,895 A | 5/1979 | Rohowetz et al. |
| 4,643,876 A | 2/1987 | Jacobs et al. |
| 4,756,758 A | 7/1988 | Lent et al. |
| 4,756,882 A | 7/1988 | Jacobs et al. |
| 4,863,627 A | 9/1989 | Davies et al. |
| 4,892,706 A | 1/1990 | Kralovic et al. |
| 4,956,145 A | 9/1990 | Cummings et al. |
| 5,053,339 A | 10/1991 | Patel |
| 5,087,659 A | 2/1992 | Fujisawa |
| 5,139,957 A | 8/1992 | Grack |
| 5,420,000 A | 5/1995 | Patel et al. |
| 5,445,792 A | 8/1995 | Rickloff et al. |
| 5,482,684 A | 1/1996 | Martens et al. |
| 5,518,927 A | 5/1996 | Malchesky et al. |
| 5,620,656 A | 4/1997 | Wensky et al. |
| 5,955,025 A | 9/1999 | Barrett |
| 5,990,199 A | 11/1999 | Bealing et al. |
| 6,063,631 A | 5/2000 | Ignacio |
| D433,511 S | 11/2000 | Nieves |
| D438,980 S | 3/2001 | Hehenberger |
| D439,344 S | 3/2001 | Henenberger |
| 6,238,623 B1 | 5/2001 | Amhof et al. |
| 6,287,518 B1 | 9/2001 | Ignacio et al. |
| 6,346,417 B1 | 2/2002 | Ignacio et al. |
| 6,348,355 B1 | 2/2002 | Bäther et al. |
| 6,352,837 B1 | 3/2002 | Witcher et al. |
| 6,488,890 B1 | 12/2002 | Kirckof |
| 6,790,411 B1 | 9/2004 | Read |
| 7,192,554 B2 | 3/2007 | Read |

FOREIGN PATENT DOCUMENTS

| | | |
|---|---|---|
| DE | 273 775 A1 | 11/1989 |
| DE | 273 776 A1 | 11/1989 |
| DE | 199 25 120 | 12/2000 |
| EP | 0 914 833 | 5/1999 |
| EP | 1 052 507 A2 | 11/2000 |
| JP | 49-046440 | 12/1974 |
| JP | 04-364174 | 12/1992 |
| JP | 11-178904 | 7/1999 |
| JP | 2003-004638 | 1/2003 |
| WO | WO 96/33242 | 10/1996 |
| WO | WO 98/46279 A1 | 10/1998 |
| WO | WO 98/46994 A1 | 10/1998 |
| WO | WO 98/52621 A1 | 11/1998 |
| WO | WO 98/58683 | 12/1998 |
| WO | WO 00/50634 A1 | 8/2000 |
| WO | WO 00/61200 A1 | 10/2000 |
| WO | WO 00/73783 A1 | 12/2000 |
| WO | WO 01/40792 A1 | 6/2001 |

OTHER PUBLICATIONS

U.S. Appl. No. 29/085,500, filed Mar. 24, 1998, Nieves.
Bishop, "Chapter 8B: Oxidation—Reduction Indicators of High Formal Potential," *Indicators*, Bishop, Ed., Pergamon Press Ltd., Braunschweig, Germany, Title page, Publication page, Table of Contents, and pp. 531-684, (1972).
Haber et al., The Catalytic Decompoistion of Hydrogen Peroxide by Iro Salts, *Proceedings of the Royal Society*, vol. 147, No. 861: Title page, Publication page, Table of Contents, and pp. 332-351, (1934).
Lillie et al., "Ch. 2: The General Nature of Dyes and Their Classification," H.J. *Conn's Biological Stains, a Handbook on the Nature and Uses of the Dyes Employed in the Biological Laboratory*, 9$^{th}$ ed., The Williams & Wilkins Company, available from the Sigma Chemical Company, St. Louis, MO, Title page, Publication page, Table of Contents, and pp. 19-32, (1977).
Nakagawa et al. "Characteristic Bleaching Profiles of Cyanine Dyes Depending on Active Oxygen Species in the Controlled Fenton Reaction," *Biol. Pharm. Bull.*, vol. 16, No. 11, pp. 1061-1064, (1993).

*Primary Examiner*—Lyle A Alexander

(57) ABSTRACT

The present invention provides a hydrogen peroxide indicator and a peracetic acid indicator that include a substrate on which is disposed an indicator composition that includes at least one of a select group of colorants and a transition metal salt. As a result of exposure to hydrogen peroxide and/or peracetic acid, the colorants change color, and even become colorless, thereby providing an indication of the presence of hydrogen peroxide and/or peracetic acid.

2 Claims, No Drawings

HYDROGEN PEROXIDE AND PERACETIC ACID INDICATORS AND METHODS

CROSS REFERENCE TO RELATED APPLICATIONS

This is a continuation of U.S. application Ser. No. 11/655,022, filed Jan. 18, 2007, issued as U.S. Pat. No. 7,670,552, which is a divisional of U.S. Ser. No. 10/037,435, filed Dec. 31, 2001, issued as U.S. Pat. No. 7,192,554, the disclosures of which are incorporated by reference in their entirety herein.

BACKGROUND OF THE INVENTION

Medical instruments, particularly surgical instruments, are typically sterilized prior to use using steam or other sterilizing/disinfecting gases or liquids. A traditional sterilization process uses steam under pressure. Alternative sterilization processes use ethylene oxide or hydrogen peroxide in vapor form as the sterilant.

The use of hydrogen peroxide and other chemical vapor phase sterilization techniques typically involve operating temperatures well below those associated with steam sterilization. These "low temperature" technologies generally operate at temperatures below about 80° C., and often below about 65° C. For hydrogen peroxide sterilization, the sterilized goods are typically available for use shortly after the completion of the sterilization cycle. This is because the decomposition products (e.g., water and oxygen) are non-toxic. The potency of the hydrogen peroxide may be augmented by the presence of electrical energy in the form of an ionizing plasma field.

An alternative sterilization process uses a liquid phase peracetic acid solution. Such sterilization processes may be performed in a sterilization chamber. During a typical sterilization cycle, an article to be sterilized is exposed to a sterilization solution containing, for example, about 2000 parts per million (ppm) to 2500 ppm of peracetic acid. The article is exposed to the solution for a sufficient time at a sufficiently high temperature, e.g., 50° C.-60° C., for the sterilization to be effective.

Sterilization indicators are used to monitor whether a sterilization process has been performed. Sterilization indicators typically include an indicator composition, carried on a substrate, that changes color during the sterilization process. Conventional indicators for hydrogen peroxide, however, often fade upon exposure to light. Thus, there is still a need for suitable indicators that include color change compositions for indicating the sterilization of articles using hydrogen peroxide or peracetic acid.

SUMMARY OF THE INVENTION

The present invention is directed to indicators and methods for detecting the presence of, and for monitoring sterilization processes utilizing, a sterilant, including a hydrogen peroxide and/or a peracetic acid sterilant. The indicators and methods include an indicator including a substrate and an indicator composition disposed thereon, wherein the indicator composition includes at least one colorant that changes color when exposed to a sterilant, at least one binder resin, and at least one salt of a transition metal.

In a preferred embodiment of the invention, the transition metal is selected from the group consisting of Group VB, Group VIII, and Group IB transition metals, and combinations thereof. The sterilization indicators of the present invention preferably include colorants that change color when exposed to hydrogen peroxide and/or peracetic acid. The sterilization indicators of the present invention preferably include a colorant selected from the group of classes of colorants consisting of Methane, Monoazo, Diazo, Triazo, Diazine, Thiazine, Xanthene, Oxazine, Cyanine, Anthraquinone, Benzodifuranone, Styryl, Phthalocyanine, Quinophthalone, Nitro, and Nitroso colorants, and combinations thereof, and/or a colorant selected from the group consisting of Victoria green S extra, Basic blue 41, Basic red 15, Acid green AX986, Keystone soap fluoro green, and Basic red 14 colorants, and combinations thereof. Therefore, a sterilization indicator of the present invention may include a colorant that includes, for instance, a combination of a Methane and a Diazo colorant, a combination of Basic blue 41 and Basic red 15, or a combination of a Methane colorant and Basic blue 41. An even more preferred sterilization indicator includes an indicator composition further including at least one colorant that does not change color when exposed to a sterilant, preferably hydrogen peroxide.

In one embodiment, the present invention is directed to methods and indicators for detecting the presence of hydrogen peroxide, preferably hydrogen peroxide in the vapor phase. The methods and indicators are particularly well suited for monitoring whether a hydrogen peroxide sterilization process has been performed.

In another embodiment, the present invention is directed to methods and indicators for detecting the presence of peracetic acid. The peracetic acid can be in the liquid phase or in the vapor phase. Preferably, the peracetic acid is in the liquid phase. The methods and indicators are well suited for monitoring whether a peracetic acid sterilization process has been performed.

The present invention provides a hydrogen peroxide indicator and a peracetic acid indicator that include a substrate and an indicator composition disposed thereon, wherein the indicator composition includes at least one colorant, at least one metal salt, and at least one binder resin. Preferably, the metal salt is a transition metal salt. More preferably, the transition metal salt includes one or more metals from Groups VIB, VIII, and IB of the Periodic Chart, including iron, copper, cobalt, and chromium. Even more preferably, the transition metal salt includes metals from Groups VIII and IB of the Periodic Chart, including iron, copper, and cobalt, and combinations thereof. Most preferably, the transition metal salt includes iron and/or copper. The salts can include inorganic or organic anions. Examples include chloride, acetate, sulfate, chromate, iodate, molybdate, nitrate, oxalate, citrate, propionate, lactate, malate, tartrate, and benzoate. Preferred anions include chloride, acetate, and sulfate.

In a preferred embodiment, the hydrogen peroxide indicator includes: at least one salt of a transition metal; at least one colorant selected from the group of classes of colorants consisting of Methane, Monoazo, Diazo, Triazo, Diazine, Thiazine, Xanthene, Oxazine, and Anthraquinone colorants, and combinations thereof, and/or at least one colorant selected from the group consisting of Victoria green S extra, Basic blue 41, Basic red 15, Acid green AX986, Keystone soap fluoro green, Basic red 14, and combinations thereof and at least one binder resin. In a more preferred embodiment, the transition metal salt is selected from the group consisting of a copper salt, a cobalt salt, an iron salt, a chromium salt, and combinations thereof. In an even more preferred embodiment, the transition metal salt is at least one iron salt. In a still more preferred embodiment, the colorant is selected from the group consisting of Patent blue violet, Alkali blue 4B, Victoria pure blue BO, Acid fuchsin sodium salt, Alphazurine A, Methyl violet 2B, Ethyl violet, FD/C blue 1, Brilliant blue R, Lissamine green B, Erioglaucine, Eriochrome black T, Eriochrome blue black B, Cibacron brilliant red 3B, Chromotrope 2B, Amaranth, D&C red No. 33, Bordeaux R, Acid violet 7, Acid violet 5, Plasmocorinth B, Acid Blue 113, Acid red 151, Acid black 24, Acid red 97, Direct red 75, Brilliant crocein MOO, Ponceau SS, Reactive black 5, Arsenazo 111, Direct blue 71, Azocarmine G, Methylene violet 3RAX, Toluidine blue O, Methylene green, Sulforhodamine B, Rhodanine 6G, Violamine R, Nile blue A, Basic blue 3, Brilliant cresyl blue BB, Basic red 15, Alizarin violet 3R, Victoria green S extra, Basic blue 41, Acid green AX986, Keystone soap fluoro green, Basic red 14, D&C green No. 5, and combinations thereof. In an even more preferred embodiment, the colorant is selected from the group consisting of Victoria pure blue BO, Acid fuchsin sodium salt, Alphazurine A, Methyl violet 2B, Ethyl violet, FD/C blue 1, Brilliant blue R, Lissamine green B, Erioglaucine, Eriochrome black T, Eriochrome blue black B, Cibacron brilliant red 3B, Chromotrope 2B, D&C red No. 33, Acid violet 7, Acid violet 5, Plasmocorinth B, Acid blue 113, Acid red 151, Acid black 24, Acid red 97, Direct red 75, Brilliant crocein MOO, Ponceau SS, Reactive black 5, Arsenazo 111, Azocarmine G, Methylene violet 3RAX, Toluidine blue O, Methylene green, Sulforhodamine B, Rhodanine 6G, Violamine R, Nile blue A, Basic blue 3, Brilliant cresyl blue BB, Basic red 15, Alizarin violet 3R, Victoria green S extra, Basic blue 41, Acid green AX986, Keystone soap fluoro green, Basic red 14, D&C green No. 5, and combinations thereof. In a still more preferred embodiment, the hydrogen peroxide indicator includes an indicator composition that further includes at least one colorant that does not change color when exposed to hydrogen peroxide vapor.

In another preferred embodiment, the hydrogen peroxide indicator includes a substrate and an indicator composition disposed thereon, wherein the indicator composition includes: at least one salt of cobalt, copper, chromium, and combinations thereof; at least one colorant that changes color when exposed to hydrogen peroxide vapor; and at least one binder resin. In a preferred embodiment, the salt is selected from the group consisting of cobalt chloride, cobalt acetate, cupric chloride, cupric sulfate, cupric acetate, chromium potassium sulfate, and combinations thereof. In another preferred embodiment, the colorant is selected from the group of classes of colorants consisting of Methane, Monoazo, Diazo, Triazo, Diazine, Thiazine, Cyanine, Xanthene, Oxazine, and Anthraquinone colorants, and combinations thereof, and/or the colorant is selected from the group consisting of Victoria green S extra, Basic blue 41, Basic red 15, Acid green AX986, Keystone soap fluoro green, Basic red 14, and combinations thereof. In a further preferred embodiment, the indicator composition additionally includes at least one colorant that does not change color when exposed to hydrogen peroxide.

In another preferred embodiment, the hydrogen peroxide indicator includes a substrate and an indicator composition disposed thereon, wherein the indicator composition includes at least one cobalt salt, at least one colorant that changes color when exposed to hydrogen peroxide vapor, and at least one binder resin. In a more preferred embodiment, the colorant is selected from the group of classes of colorants consisting of Methane, Monoazo, Diazo, Oxazine, and Anthraquinone colorants, and combinations thereof. In an even more preferred embodiment, the colorant is selected from the group consisting of Patent blue violet, Aniline blue, Erioglaucine, Arsenazo 1, Acid blue 92, Eriochrome blue black B, Congo red, Acid blue 29, Nile blue A, Reactive blue 2, Basic red 15, D&C green No. 5, and combinations thereof.

In another preferred embodiment, the hydrogen peroxide indicator includes a substrate and an indicator composition disposed thereon, wherein the indicator composition includes at least one copper salt, at least one colorant that changes color when exposed to hydrogen peroxide vapor, and at least one binder resin. In a more preferred embodiment, the colorant is selected from the group of classes of colorants consisting of Methane, Monoazo, Diazo, Triazo, Diazine, Thiazine, Xanthene, Oxazine, Cyanine, and Anthraquinone colorants, and combinations thereof, and/or the colorant is selected from the group consisting of Victoria green S extra, Basic blue 41, Basic red 15, Acid green AX986, Keystone soap fluoro green, Basic red 14, and combinations thereof. In an even more preferred embodiment, the colorant is selected from the group consisting of Alphazurine A, Methyl violet 2B, Ethyl violet, FD/C blue 1, Brilliant blue R, Lissamine green B, Erioglaucine, Victoria pure blue BO, Acid fuchsin sodium salt, Patent blue violet, Guinea green B, Coomassie violet R 150, Mordant brown 48, Chromotrope 2B, D&C red No. 33, Bordeaux R, Acid violet 7, Acid violet 5, Plasmocorinth, Acid red 151, Acid blue 29, Acid black 24, Acid red 97, Direct red 75, Brilliant crocein MOO, Ponceau SS, Reactive black 5, Arsenazo 111, Direct blue 71, Azocarmine G, Methylene violet 3RAX, Toluidine blue O, Azure B, Methylene green, Sulforhodamine B, Rhodanine 6G, Violamine R, Nile blue A, Basic blue 3, Brilliant cresyl blue BB, Quinaldine red, Basic red 15, Alizarin violet 3R, Reactive blue 2, Victoria green S extra, Basic blue 41, Acid green AX986, Keystone soap fluoro green, Basic red 14, D&C green No. 5, Fast green FCF, and combinations thereof. In a still more preferred embodiment, the colorant is selected from the group of classes of colorants consisting of Methane, Monoazo, Diazo, Diazine, Thiazine, Xanthene, Oxazine, and Cyanine colorants, and combinations thereof, and/or the colorant is selected from the group consisting of Victoria green S extra, Basic blue 41, Basic red 15, Acid green AX986, Keystone soap fluoro green, Basic red 14, and combinations thereof. In a most preferred embodiment, the colorant is selected from the group consisting of Alphazurine A, Methyl violet 2B, Ethyl violet, FD/C blue 1, Brilliant blue R, Lissamine green B, Erioglaucine, Victoria pure blue BO, Acid fuchsin sodium salt, Coomassie violet R 150, Mordant brown 48, Acid violet 5, Plasmocorinth, Acid red 151, Acid blue 29, Acid black 24, Acid red 97, Direct red 75, Arsenazo 111, Azocarmine G, Methylene violet 3RAX, Toluidine blue O, Methylene green, Rhodanine 6G, Basic blue 3, Brilliant cresyl blue BB, Quinaldine red, Basic red 15, Reactive blue 2, Victoria green S extra, Basic blue 41, Keystone soap fluoro green, Basic red 14, D&C green No. 5, and combinations thereof.

In another preferred embodiment, the hydrogen peroxide indicator includes a substrate and an indicator composition disposed thereon, wherein the indicator composition includes at least one chromium salt, at least one colorant that changes color when exposed to hydrogen peroxide vapor, and at least one binder resin. In a more preferred embodiment, the colorant is selected from the group of classes of colorants consisting of Methane, Monoazo, Diazo, and Cyanine colorants, and combinations thereof. In an even more preferred embodiment, the colorant is selected from the group consisting of Ethyl violet, Eriochrome black T, Eriochrome blue black B, Congo red, Acid blue 113, Quinaldine red, and combinations thereof. In a still more preferred embodiment, the colorant is selected from the group consisting of Ethyl violet, Eriochrome black T, Eriochrome blue black B, Acid blue 113, Quinaldine red, and combinations thereof.

In another embodiment, the present invention provides a peracetic acid indicator that includes a substrate and an indicator composition disposed thereon, wherein the indicator composition includes: at least one transition metal salt; at least one colorant selected from the group of classes of colorants consisting of Monoazo and Diazo colorants, and combinations thereof, and/or at least one colorant selected from the group consisting of Victoria green S extra, Basic blue 41, Basic red 15, Acid green AX986, Keystone soap fluoro green, Basic red 14, and combinations thereof; and at least one binder resin. In a preferred embodiment the indicator composition further includes at least one colorant that does not change color when exposed to peracetic acid.

In a preferred embodiment, the peracetic acid indicator includes a substrate and an indicator composition disposed thereon, wherein the indicator composition includes: at least one salt of copper, cobalt, and combinations thereof; at least one colorant that changes color when exposed to peracetic acid, preferably liquid peracetic acid; and at least one binder resin. In a more preferred embodiment, the indicator composition further includes at least one colorant that does not change color when exposed to peracetic acid.

In another preferred embodiment, the peracetic acid indicator includes a substrate and an indicator composition disposed thereon, wherein the indicator composition includes at least one copper salt, at least one colorant that changes color when exposed to peracetic acid, preferably liquid peracetic acid, and at least one binder resin. In a more preferred embodiment, the colorant is selected from the group of classes of colorants consisting of Monoazo and Diazo colorants, and combinations thereof, and/or the colorant is selected from the group consisting of Victoria green S extra, Basic blue 41, Basic red 15, Acid green AX986, Keystone soap fluoro green, Basic red 14, and combinations thereof. In an even more preferred embodiment, the colorant is selected from the group consisting of Acid violet 7, Evans blue, Naphthol blue black, Reactive black 5, Brilliant black BN, Azocarmine B, and combinations thereof.

In another preferred embodiment, the peracetic acid indicator includes a substrate and an indicator composition disposed thereon, wherein the indicator composition includes at least one cobalt salt, at least one colorant that changes color when exposed to peracetic acid, preferably liquid peracetic acid, and at least one binder resin. In a more preferred embodiment, the colorant is selected from the group of classes of colorants consisting of Monoazo and Diazo colorants, and combinations thereof. In an even more preferred embodiment, the colorant is selected from the group consisting of Cibacron brilliant red 3B, Evans blue, Reactive black 5, Brilliant black BN, and combinations thereof.

The invention also provides methods of monitoring a sterilization process, including a hydrogen peroxide sterilization process and a peracetic acid sterilization process. These methods include: providing an indicator including an indicator composition including at least one salt of a transition metal, at least one colorant that changes color when exposed to a sterilant, and at least one binder resin; providing an article to be sterilized; and exposing the article to be sterilized and the indicator to a sterilant. The sterilant preferably includes hydrogen peroxide, preferably hydrogen peroxide vapor and/or peracetic acid, preferably liquid peracetic acid.

A method of monitoring a hydrogen peroxide sterilization process of the present invention includes: providing a hydrogen peroxide indicator including a substrate and an indicator composition disposed thereon that includes at least one salt of a transition metal, at least one colorant selected from the group of classes of colorants consisting of Methane, Monoazo, Diazo, Triazo, Diazine Thiazine, Cyanine, Xanthene, Oxazine, Anthraquinone, Benzodifuranone, Styryl, Phthalocyanine, Quinophthalone, Nitro, and Nitroso colorants, and combinations thereof, and/or at least one colorant selected from the group consisting of Victoria green S extra, Basic blue 41, Basic red 15, Acid green AX986, Keystone soap fluoro green, Basic red 14, and combinations thereof, and at least one binder resin; providing an article to be sterilized; and exposing the hydrogen peroxide indicator and the article to be sterilized to hydrogen peroxide vapor. In a more preferred method, the salt of a transition metal is selected from the group consisting of cupric chloride, ferrous chloride, cobalt chloride, cobalt acetate, cupric sulfate, ferrous sulfate, chromium potassium sulfate, cupric acetate, and combinations thereof. In an even more preferred method, the indicator composition further includes a colorant that does not change color when exposed to hydrogen peroxide vapor.

In a preferred method of the present invention, the method includes: providing a hydrogen peroxide indicator including a substrate and an indicator composition disposed thereon that includes at least one salt of copper, chromium, iron, cobalt, and combinations thereof, at least one colorant that changes color when exposed to hydrogen peroxide vapor, and at least one binder resin; providing an article to be sterilized; and exposing the hydrogen peroxide indicator and the article to be sterilized to hydrogen peroxide vapor. In a more preferred method, the colorant is selected from the group of classes of colorants consisting of Methane, Monoazo, Diazo, Triazo, Diazine, Thiazine Cyanine, Xanthene, Oxazine, and Anthraquinone colorants, and combinations thereof, and/or the colorant is selected from the group consisting of Victoria green S extra, Basic blue 41, Basic red 15, Acid green AX986, Keystone soap fluoro green, Basic red 14, and combinations thereof.

Another preferred method includes providing a hydrogen peroxide indicator including a substrate and an indicator composition disposed thereon that includes at least one cobalt salt, at least one colorant that changes color when exposed to hydrogen peroxide vapor, and at least one binder resin, providing an article to be sterilized, and exposing the hydrogen peroxide indicator and the article to be sterilized to hydrogen peroxide vapor. In a more preferred method, the colorant is selected from the group of classes of colorants consisting of Methane, Monoazo, Diazo, Oxazine, and Anthraquinone colorants, and combinations thereof. In an even more preferred method, the colorant is selected from the group consisting of Patent blue violet, Aniline blue, Erioglaucine, Arsenazo 1, Acid blue 92, Eriochrome blue black B, Congo red, Acid blue 29, Nile blue A, Reactive blue 2, Basic red 15, D&C green No. 5, and combinations thereof.

Another preferred method includes providing a hydrogen peroxide indicator including a substrate and an indicator composition disposed thereon that includes at least one copper salt, at least one colorant that changes color when exposed to hydrogen peroxide vapor, and at least one binder resin, providing an article to be sterilized, and exposing the hydrogen peroxide indicator and the article to be sterilized to hydrogen peroxide vapor. In a more preferred method, the colorant is selected from the group of classes of colorants consisting of Methane, Monoazo, Diazo, Triazo, Diazine, Thiazine, Xanthene, Oxazine, Cyanine, and Anthraquinone colorants, and combinations thereof, and/or the colorant is selected from the group consisting of Victoria green S extra, Basic blue 41, Basic red 15, Acid green AX986, Keystone soap fluoro green, Basic red 14, and combinations thereof. In an even more preferred method, the colorant is selected from the group consisting of Alphazurine A, Methyl violet 2B, Ethyl violet, FD/C blue 1, Brilliant blue R, Lissamine green B, Erioglaucine, Victoria pure blue BO, Acid fuchsin sodium salt, Patent blue violet, Guinea green B, Coomassie violet R 150, Mordant brown 48 Chromotrope 2B, D&C red No. 33, Bordeaux R, Acid violet 7, Acid violet 5, Plasmocorinth, Acid red 151, Acid blue 29, Acid black 24, Acid red 97, Direct red 75, Brilliant crocein MOO, Ponceau SS, Reactive black 5, Arsenazo 111, Direct blue 71, Azocarmine G, Methylene violet 3RAX, Toluidine blue O, Azure B, Methylene green, Sulforhodamine B, Rhodanine 6G, Violamine R, Nile blue A, Basic blue 3, Brilliant cresyl blue BB, Quinaldine red, Basic red 15, Alizarin violet 3R, Reactive blue 2, Victoria green S extra, Basic blue 41, Acid green AX986, Keystone soap fluoro green, Basic red 14, D&C green No. 5, Fast green FCF, and combinations thereof. In a still more preferred method, the colorant is selected from the group consisting of Alphazurine A, Methyl violet 2B, Ethyl violet, FD/C blue 1, Brilliant blue R, Lissamine green B, Erioglaucine, Victoria pure blue BO, Acid fuchsin sodium salt, Coomassie violet R 150, Mordant brown 48, Acid violet 5, Plasmocorinth, Acid red 151, Acid blue 29, Acid black 24, Acid red 97, Direct red 75, Arsenazo 111, Azocarmine G, Methylene violet 3RAX, Toluidine blue O, Methylene green, Rhodanine 6G, Basic blue 3, Brilliant cresyl blue BB, Quinaldine red, Basic red 15, Reactive blue 2, Victoria green S extra, Basic blue 41, Keystone soap fluoro green, Basic red 14, D&C green No. 5, and combinations thereof.

Another preferred method includes providing a hydrogen peroxide indicator including a substrate and an indicator composition disposed thereon that includes at least one iron salt, at least one colorant that changes color when exposed to hydrogen peroxide vapor, and at least one binder resin, providing an article to be sterilized, and exposing the hydrogen peroxide indicator and the article to be sterilized to hydrogen peroxide vapor. In a more preferred method, the colorant is selected from the group of classes of colorants consisting of Methane, Monoazo, Diazo, Triazo, Diazine, Thiazine, Cyanine, Xanthene, Oxazine, and Anthraquinone colorants, and combinations thereof, and/or the colorant is selected from the group consisting of Victoria green S extra, Basic blue 41, Basic red 15, Acid green AX986, Keystone soap fluoro green, Basic red 14, and combinations thereof. In an even more preferred method, the colorant is selected from the group consisting of Patent blue violet, Alkali blue 4B, Victoria pure blue BO, Acid fuchsin sodium salt, Alphazurine A, Methyl violet 2B, Ethyl violet, FD/C blue 1, Brilliant blue R, Lissamine green B, Erioglaucine, Eriochrome black T, Eriochrome blue black B, Cibacron brilliant red 3B, Chromotrope 2B, Amaranth, D&C red No. 33, Bordeaux R, Acid violet 7, Acid violet 5, Plasmocorinth B, Acid blue 113, Acid red 151, Acid black 24, Acid red 97, Direct red 75, Brilliant crocein MOO, Ponceau SS, Reactive black 5, Arsenazo 111, Direct blue 71, Azocarmine G, Methylene violet 3RAX, Toluidine blue O, Methylene green, Sulforhodamine B, Rhodanine 6G, Violamine R, Nile blue A, Basic blue 3, Brilliant cresyl blue BB, Quinaldine red, Basic red 15, Alizarin violet 3R, Victoria green S extra, Basic blue 41, Acid green AX986, Keystone soap fluoro green, Basic red 14, D&C green No. 5, and combinations thereof. In a still more preferred method, the colorant is selected from the group consisting of Victoria pure blue BO, Acid fuchsin sodium salt, Alphazurine A, Methyl violet 2B, Ethyl violet, FD/C blue 1, Brilliant blue R, Lissamine green B, Erioglaucine, Eriochrome black T, Eriochrome blue black B, Cibacron brilliant red 3B, Chromotrope 2B, D&C red No. 33, Acid violet 7, Acid violet 5, Plasmocorinth B, Acid blue 113, Acid red 151, Acid black 24, Acid red 97, Direct red 75, Brilliant crocein MOO, Ponceau SS, Reactive black 5, Arsenazo 111, Azocarmine G, Methylene violet 3RAX, Toluidine blue O, Methylene green, Sulforhodamine B, Rhodanine 6G, Violamine R, Nile blue A, Basic blue 3, Brilliant cresyl blue BB, Basic red 15, Alizarin violet 3R, Victoria green S extra, Basic blue 41, Acid green AX986, Keystone soap fluoro green, Basic red 14, D&C green No. 5, and combinations thereof.

Another preferred method includes providing a hydrogen peroxide indicator including a substrate and an indicator composition disposed thereon that includes at least one chromium salt, at least one colorant that changes color when exposed to hydrogen peroxide vapor, and at least one binder resin, providing an article to be sterilized, and exposing the hydrogen peroxide indicator and the article to be sterilized to hydrogen peroxide vapor. In a more preferred method, the colorant is selected from the group of classes of colorants consisting of Methane, Monoazo, Diazo, and Cyanine colorants, and combinations thereof. In an even more preferred method, the colorant is selected from the group consisting of Ethyl violet, Eriochrome black T, Eriochrome blue black B, Congo red, Acid blue 113, Quinaldine red, and combinations thereof. In a still more preferred method, the colorant is selected from the group consisting of Ethyl violet, Eriochrome black T, Eriochrome blue black B, Acid blue 113, Quinaldine red, and combinations thereof.

A preferred method of monitoring a sterilization process of the present invention includes: providing a peracetic acid indicator including a substrate and an indicator composition disposed thereon that includes at least one salt of a transition metal, at least one colorant selected from the group of classes of colorants consisting of Monoazo, Diazo, Benzodifuranone, Styryl, Phthalocyanine, Quinophthalone, Nitro, and Nitroso colorants, and combinations thereof, and/or at least one colorant selected from the group consisting of Victoria green S extra, Basic blue 41, Basic red 15, Acid green AX986, Keystone soap fluoro green, Basic red 14, and combinations thereof, and at least one binder resin; providing an article to be sterilized; and exposing the peracetic acid indicator and the article to be sterilized to peracetic acid, preferably liquid peracetic acid. In a more preferred method, the salt of a transition metal is selected from the group consisting of cupric acetate, cobalt acetate, cupric sulfate, and combinations thereof.

In a preferred method of the present invention, the method includes: providing a peracetic acid indicator including a substrate and an indicator composition disposed thereon that includes at least one salt of copper, cobalt, and combinations thereof, at least one colorant that changes color when exposed to peracetic acid, and at least one binder resin; providing an article to be sterilized; and exposing the peracetic acid indicator and the article to be sterilized to peracetic acid, preferably liquid peracetic acid. In a more preferred method, the colorant is selected from the group of classes of colorants consisting of Monoazo and Diazo colorants, and combinations thereof, and/or the colorant is selected from the group consisting of Victoria green S extra, Basic blue 41, Basic red 15, Acid green AX986, Keystone soap fluoro green, Basic red 14, and combinations thereof.

In a preferred method of the present invention, the method includes: providing a peracetic acid indicator including a substrate and an indicator composition disposed thereon that includes at least one copper salt, at least one colorant that changes color when exposed to peracetic acid, and at least one binder resin; providing an article to be sterilized; and exposing the peracetic acid indicator and the article to be sterilized to peracetic acid, preferably liquid peracetic acid. In a more preferred method, the colorant is selected from the group of classes of colorants consisting of Monoazo and Diazo colorants, and combinations thereof, and/or the colorant is selected from the group consisting of Victoria green S extra, Basic blue 41, Basic red 15, Acid green AX986, Keystone soap fluoro green, Basic red 14, and combinations thereof. In a still more preferred method, the colorant is selected from the group consisting of Acid violet 7, Evans blue, Naphthol blue black, Reactive black 5, Brilliant black BN, Azocarmine B, and combinations thereof.

In another preferred method of the present invention, the method includes: providing a peracetic acid indicator including a substrate and an indicator composition disposed thereon that includes at least one cobalt salt, at least one colorant that changes color when exposed to peracetic acid, and at least one binder resin; providing an article to be sterilized; and exposing the peracetic acid indicator and the article to be sterilized to peracetic acid preferably liquid peracetic acid. In a more preferred method, the colorant is selected from the group consisting of Monoazo and Diazo colorants and combinations thereof. In a still more preferred method, the colorant is selected from the group consisting of Cibacron brilliant red 3B, Evans blue, Reactive black 5, Brilliant black BN, and combinations thereof.

DETAILED DESCRIPTION OF PREFERRED EMBODIMENTS

In one embodiment, the present invention provides a sterilant indicator that includes a substrate on which is disposed an indicator composition that includes at least one metal salt, preferably a transition metal salt, at least one of a select group of colorants, and at least one binder resin. Preferably, the sterilant is hydrogen peroxide and/or peracetic acid. As a result of exposure to a sterilant, the colorants change color, and even become colorless, thereby providing an indication of the presence of the sterilant and a method for monitoring a sterilization process.

One embodiment of the invention provides a hydrogen peroxide indicator that includes a substrate on which is disposed an indicator composition that includes at least one transition metal salt and at least one of a select group of colorants that changes color when exposed to hydrogen peroxide, and at least one binder resin. As a result of exposure to hydrogen peroxide, the colorants change color, and even become colorless, providing an indication of hydrogen peroxide presence.

In another embodiment, the present invention provides a peracetic acid indicator that includes a substrate on which is disposed an indicator composition that includes at least one metal salt, preferably a transition metal salt, at least one of a select group of colorants that changes color when exposed to peracetic acid, and at least one binder resin. As a result of exposure to peracetic acid, the colorants change color, thereby providing an indication of the presence of peracetic acid.

In particular, the present invention is directed to a system for indicating exposure to a hydrogen peroxide vapor sterilization process or a peracetic acid sterilization process, which may use either liquid peracetic acid or peracetic acid vapor. In one embodiment, the indicator composition includes at least one component that is transformed (typically, chemically transformed) when exposed to hydrogen peroxide vapor such that the color of the composition changes. In another embodiment, the indicator composition includes at least one component that is transformed (typically, chemically transformed) when exposed to liquid peracetic acid and/or peracetic acid vapor, preferably liquid peracetic acid, such that the color of the composition changes. The compositions may include one or more components that change color when exposed to hydrogen peroxide and/or peracetic acid, as well as other components that do not change color when exposed to hydrogen peroxide and/or peracetic acid. The composition preferably includes a polymeric binder resin to aid in applying the composition to a suitable substrate.

Indicators of the present invention are very useful to show when an article has been exposed to hydrogen peroxide and/or peracetic acid. Significantly, indicators of the present invention offer one a simple, yet effective means for indicating when a particular article has been subjected to sterilization using hydrogen peroxide vapor and/or liquid peracetic acid or peracetic acid vapor.

Preferably, the hydrogen peroxide indicator compositions of the present invention undergo a color change when exposed to an atmosphere above an aqueous solution containing 30 weight percent (wt-%) hydrogen peroxide at 50° C. within a period of at least about one hour and/or a color change when exposed to an atmosphere containing about 6 milligrams/liter (mg/l) to about 7 mg/l hydrogen peroxide (in an empty chamber, i.e., without articles to be sterilized) at a pressure of about $8 \times 10^2$ Pascals (Pa) to about $13.3 \times 10^2$ Pa and a temperature of about 45° C. to about 50° C. for a period of at least about 50 minutes, which are typical conditions within an empty commercial hydrogen peroxide plasma sterilizer. More preferably, for use in conventional sterilizers, the hydrogen peroxide indicator compositions of the present invention undergo a color change when exposed to an atmosphere containing about 6 mg/l to about 7 mg/l hydrogen peroxide (in an empty chamber) at a pressure of about $8 \times 10^2$ Pa to about $13.3 \times 10^2$ Pa and a temperature of about 45° C. to about 50° C. for a period of at least about 50 minutes. As used herein, a color change includes a change in color that is detectable by the unaided eye, including becoming colorless.

The peracetic acid indicator compositions of the present invention preferably undergo a color change when exposed to liquid and/or vapor phase peracetic acid. Preferably, the peracetic acid indicators undergo a distinct color change when exposed to an atmosphere containing at least 5% peracetic acid at room temperature for at least 5 to 10 minutes. More preferably, the indicator compositions of the present invention undergo a color change when exposed to liquid peracetic acid at a concentration of between about 100 ppm to about 10,000 ppm at temperatures between about 0° C. to about 100° C. for between about 1 second to about 15 minutes. As used herein, a color change includes a change in color that is detectable by the unaided eye, including becoming colorless.

Preferably, the indicator compositions do not significantly fade upon exposure to room lighting, e.g., fluorescent lighting. More preferably, the indicator compositions do not significantly fade, for example, upon exposure to sunlight through a window for one week or room lighting for two months.

Colorants suitable for use in the indicator compositions of the present invention include colorants classified as Methane, Monoazo, Diazo, Triazo, Diazine, Cyanine, Thiazine, Xanthene, Oxazine, Anthraquinone, Benzodifuranone, Styryl, Phthalocyanine, Quinophthalone, Nitro, and Nitroso colorants, and combinations thereof, and/or colorants including Victoria green S extra, Basic blue 41, Basic red 15, Acid green AX986, Keystone soap fluoro green, and Basic red 14 colorants, and combinations thereof. Suitable colorants for use in the indicator compositions of the present invention further include Alphazurine A, Methyl violet 2B, Ethyl violet, FD/C blue 1, Brilliant blue R, Lissamine green B, Erioglaucine, Patent blue violet, Aniline blue, Victoria pure blue BO, Acid fuchsin sodium salt, Guinea green B, Alkali blue 4B, Coomassie violet R 150, Chromotrope 2B, D & C red No. 33, Bordeaux R, Acid violet 7, Acid violet 5, Plasmocorinth B, Cibacron brilliant red 3B, Amaranth, Arsenazo 1, Acid blue 92, Eriochrome blue black B, Eriochrome black T, Mordant brown 48, Acid black 24, Acid red 97, Direct red 75, Brilliant crocein MOO, Ponceau SS, Reactive black 5, Arsenazo 111, Congo red, Acid blue 29, Acid blue 113, Acid red 151, Direct blue 71, Azocarmine G, Methylene violet 3RAX, Toluidine blue O, Methylene green, Azure B, Sulforhodamine B, Rhodanine 6G, Violamine R, Nile blue A, Basic blue 3, Brilliant cresyl blue BB, Quinaldine red, Basic red 15, Alizarin violet 3R, Reactive blue 2, Victoria green S extra, Basic blue 41, Acid green AX986, D & C green No. 5, Keystone soap fluoro green, Basic red 14, Brilliant black BN, Evans blue, Naphthol blue black, Xylidine ponceau 2R, Azocarmine B, and Fast green FCF. Alternative names and Color Index Numbers for these colorants are listed in Tables 1-13 below. Those colorants with classifications and/or Color Index Numbers that are difficult to determine are indicated in the tables as "Not Known." In this instance, "Not Known" means merely that determination of Colorant Class and/or Color Index Number is difficult, not necessarily that it is entirely unknown in the art. Various combinations of these colorants can be used in the indicator compositions of the present invention. Such mixtures or blends would increase the options available in color changes dramatically.

For hydrogen peroxide indicators, suitable colorants become colorless or change to a different color, detectable by the unaided eye, upon exposure to hydrogen peroxide vapor under conventional sterilization conditions (e.g., 6 mg/1 to about 7 mg/1 hydrogen peroxide in an empty chamber at a pressure of about $8 \times 10^2$ Pa to about $13.3 \times 10^2$ Pa and a temperature of about 45° C. to about 50° C. for a period of at least about 50 minutes) or to the more concentrated hydrogen peroxide vapors in a desiccator.

Preferably, at least one colorant is present in a hydrogen peroxide indicator composition in an amount sufficient to cause a visibly apparent color change when the composition is exposed to an atmosphere above an aqueous solution containing 30 wt-% hydrogen peroxide at 50° C. within a period of at least about one hour and/or an amount sufficient to cause a color change when exposed to an atmosphere containing about 6 mg/1 to about 7 mg/1 hydrogen peroxide (in an empty chamber) at a pressure of about $8 \times 10^2$ Pa to about $13.3 \times 10^2$ Pa and a temperature of about 45° C. to about 50° C. for a period of at least about 50 minutes. Generally, the compositions contain about 0.1 wt-% to about 5.0 wt-%, based on the total weight of the composition, of a colorant that changes color upon exposure to hydrogen peroxide.

In effect, the colorant concentration should be such as to allow a clear visual indication of a color change. Preferred are those colorants that show contrast between initial color and the color after exposure to hydrogen peroxide vapor. Examples include hydrogen peroxide indicators including cupric chloride and Alphazurine A, Methyl violet 2B, Ethyl violet, FD/C blue 1, Brilliant blue R, Lissamine green B, Erioglaucine, Victoria pure blue BO, Acid fuchsin sodium salt, Chromotrope 2B, D&C red No. 33, Bordeaux R, Acid violet 7, Acid violet 5, Plasmocorinth B, Acid black 24, Acid red 97, Direct red 75, Brilliant crocein MOO, Ponceau SS, Reactive black 5, Arsenazo 111, Direct blue 71, Azocarmine G, Methylene violet 3RAX, Toluidine blue O, Methylene green, Sulforhodamine B, Rhodanine 6G, Violamine R, Nile blue A, Basic blue 3, Brilliant cresyl blue BB, Quinaldine red, Basic red 15, Alizarin violet 3R, Victoria green S extra, Basic blue 41, Acid green AX986, Keystone soap fluoro green, Basic red 14, D & C green No. 5, and combinations thereof (Tables 1b and 5); hydrogen peroxide indicators including cupric sulfate and Patent blue violet, Guinea green B, Methylene violet 3RAX, Azure B, Basic Red 15, Fast green FCF, and combinations thereof (Table 6); and hydrogen peroxide indicators including cupric acetate and Coomassie violet R 150, Mordant brown 48, Acid red 151, Acid blue 29, Reactive blue 2, and combinations thereof (Table 10).

If at least one colorant that does not change color upon exposure to hydrogen peroxide is used in the indicator compositions of the present invention, it is present, alone or in combination with one or more additional colorants, in an amount sufficient to provide the targeted color intensity, both prior to and subsequent to exposure to hydrogen peroxide vapor. Generally, such compositions contain about 0.1 wt-% to about 5.0 wt-%, based on the total weight of the composition, of a colorant that does not change color upon exposure to hydrogen peroxide.

Such colorants that become substantially colorless after exposure to hydrogen peroxide acid can also be used in combination with other colorants (e.g., dyes or pigments) that do not change color when exposed to hydrogen peroxide to give a chemical indicator with a suitable contrasting color change by subtracting color. For example, an indicator including the metal salt cupric chloride with Cibacron brilliant red 3B (pale pink, Table 1b, No. 15) and Ethyl violet (blue, Table 1b, No. 5) would have a blue green color, as a result of the mixture of pale pink and blue. When exposed to hydrogen peroxide vapor, the Ethyl violet turns colorless (Table 1b, No. 5), leaving the pale pink of the Cibacron brilliant red 3B, which does not change color when exposed to hydrogen peroxide vapor (Table 1b, No. 15).

Preferred are those colorants that have an initial color and turns colorless after exposure to hydrogen peroxide vapor. Examples include hydrogen peroxide indicators including ferrous chloride and Alphazurine A, Methyl violet 2B, Ethyl violet, FD/C blue 1, Brilliant blue R, Lissamine green B, Erioglaucine, Victoria pure blue BO, Acid fuchsin sodium salt, Cibacron brilliant red 3B, Chromotrope 2B, D&C red No. 33, Acid violet 7, Acid violet 5, Plasmocorinth B, Acid black 24, Acid red 97, Direct red 75, Brilliant crocein MOO, Ponceau SS, Reactive black 5, Arsenazo 111, Azocarmine G, Methylene violet 3RAX, Toluidine blue O, Methylene green, Sulforhodamine B, Rhodanine 6G, Violamine R, Nile blue A, Basic blue 3, Brilliant cresyl blue BB, Basic red 15, Alizarin violet 3R, Victoria green S extra, Basic blue 41, Acid green AX986, Keystone soap fluoro green, Basic red 14, D & C green No. 5, and combinations thereof (Tables 2 and 7); hydrogen peroxide indicators including ferrous sulfate and Eriochrome black T, Eriochrome blue black B, Acid blue 113, Acid red 151, and combinations thereof (Table 8); hydrogen peroxide indicators including cupric chloride and Alphazurine A, Methyl violet 2B, Ethyl violet, FD/C blue 1, Brilliant blue R, Lissamine green B, Erioglaucine, Victoria pure blue BO, Acid fuchsin sodium salt, Acid violet 5, Plasmocorinth B, Acid black 24, Acid red 97, Direct red 75, Arsenazo 111, Azocarmine G, Methylene violet 3RAX, Toluidine blue O, Methylene green, Rhodanine 6G, Basic blue 3, Brilliant cresyl blue BB, Quinaldine red, Basic red 15, Victoria green S extra, Basic blue 41, Keystone soap fluoro green, Basic red 14, D & C green No. 5, and combinations thereof (Tables 1b and 5); hydrogen peroxide indicators including cobalt chloride and Patent blue violet, Aniline blue, Arsenazo 1, Acid blue 92, Congo red, Acid blue 29, and combinations thereof (Table 3b); hydrogen peroxide indicators including cobalt acetate and Erioglaucine, Eriochrome blue black B, Nile blue A, Reactive blue 2, Basic red 15, D&C green No. 5, and combinations thereof (Table 4); hydrogen peroxide indicators including cupric sulfate and Methylene violet 3RAX (Table 6); hydrogen peroxide indicators including chromium potassium sulfate and Ethyl violet, Eriochrome black T, Eriochrome blue black B, Acid blue 113, Quinaldine red, and combinations thereof (Table 9); and hydrogen peroxide indicators including cupric acetate and Coomassie violet R 150 (Table 10).

For peracetic acid indicators, suitable colorants change to a different color upon exposure to liquid peracetic acid under conventional sterilization conditions. The peracetic acid indicator compositions of the present invention preferably undergo a color change when exposed to liquid and/or vapor phase peracetic acid. Preferably, the peracetic acid indicators undergo a distinct color change when exposed to an atmosphere containing at least 5% peracetic acid at room temperature for at least 5 to 10 minutes. More preferably, the indicator compositions of the present invention undergo a color change when exposed to liquid peracetic acid at a concentration of between about 100 ppm to about 10,000 ppm at temperatures between about 0° C. to about 100° C. for between about 1 second to about 15 minutes.

Preferably, at least one colorant is present in a peracetic acid indicator composition in an amount sufficient to cause a visibly apparent color change when the composition is exposed in a sterilization chamber to a sterilant including liquid peracetic acid at a concentration of 0.2 percent and a pH of 6.4 for about 12 minutes at a temperature of between about 50° C. to about 56° C. The colorant concentration should be such as to allow a clear visual indication of a color change detectable by the unaided eye. Preferred colorants for peracetic acid indicators are those colorants that show contrast between the initial color and the color after exposure to liquid peracetic acid vapor. Examples include peracetic acid indicators including cupric acetate and Evans blue, Acid violet 7, Naphthol blue black, Reactive black 5, Brilliant black BN, Azocarmine B, and combinations thereof (Table 11); peracetic acid indicators including cobalt acetate and Cibacron brilliant red 3B, Evans blue, Reactive black 5, Brilliant black BN, and combinations thereof (Table 12); and peracetic acid indicators including cupric sulfate and Evans blue, Acid violet 7, Naphthol blue black, Reactive black 5, Brilliant black BN, Azocarmine B, and combinations thereof (Table 13).

Preferably, hydrogen peroxide indicators and peracetic acid indicators of the present invention include a metal salt. Preferably the metal salt is a transition metal salt. More preferably, the metal salt includes one or more metals from Groups VIB, VIII, and IB of the Periodic Chart, which include iron, copper, cobalt, and chromium. Even more preferably, the metal salt includes metals from Groups VIII and IB of the Periodic Chart, which include iron, copper, cobalt, and combinations thereof. Most preferably, the metal salt includes iron and/or copper.

The salts can include inorganic or organic anions. Examples include chloride, acetate, sulfate, chromate, iodate, molybdate, nitrate, oxalate, citrate, propionate, lactate, malate, tartrate, and benzoate. Preferred anions include chloride, acetate, and sulfate.

The indicator composition is generally formulated in the form of a dispersion or solution in water or an organic solvent (preferably, an organic solvent). The composition includes at least one colorant as described above as well as an organic binder resins. A wide variety of suitable binder resins can be used. Examples include synthetic or natural polymers or resins. Suitable binder resins are those that do not interfere with the function of the indicator composition. Examples include cellulose acetate butyrate, cellulose acetate propionate, hydroxypropyl cellulose, nitrocellulose, urethane alkyd, epoxy, alkylated urea- and melamine-formaldehyde, polyamide, styrene butadiene, vinyl, phenolic, shellac, ethyl cellulose, methyl cellulose, acrylic, and ultraviolet and electron beam curable resins. A sufficient amount of binder resin is included in the compositions to provide adequate binding of the composition to a substrate on which it is disposed, while providing the desired rate of color change. Generally, the compositions contain about 20 wt-% to about 40 wt-% of a polymer binder resin, based on the total weight of the composition.

Indicator compositions of the present invention can also include other resins that do not necessarily function as a binder resin. For example, the compositions can include a resin that functions as a dispersing agent, such as Rhoplex I-545, a water based acrylic polymer, available from Rohm and Haas Corp., Philadelphia, Pa., that assists in dispersing the ingredients of the composition in the solvent used in application of the composition to a substrate. Indicator compositions of the present invention can also include opacifying agents such as titanium dioxide, surfactants, plasticizers, antifoam agents, and the like. For certain embodiments, a basic material such as an organic amine (e.g., triethanolamine) can be used to enhance sensitivity of the colorant to the low concentration of hydrogen peroxide in a conventional sterilizer. Typically, such additives are used in no more than about 5 wt-% based on the total weight of the indicator composition.

The compositions are typically applied to a substrate out of a solvent as discussed above. Suitable solvents include water and organic solvents such as ketones, esters, alcohols, and the like. Examples of suitable solvents include methyl ethyl ketone, n-propyl acetate, and isopropanol. The solvent is typically used in an amount of up to about 20 wt-%, based on the total weight of the composition. The indicator composition can be applied to the substrate by a wide variety of techniques, including, for example, printing or coating by flexographic, gravure, screen, or die processes.

The substrate on which the indicator composition is disposed can be any of a wide variety. Typically, suitable substrates include polymeric materials, which may be pigmented or colorless, such as polyester, polyethylene, or polystyrene films, nonwovens, paper, and the like. Preferably, it is a plastic polystyrene backing (commercially available from Plastic Suppliers, Inc., Chicago Heights, Ill.). The substrate may be in the form of a strip of material (e.g., a strip of material having the dimensions 2 cm by 13 cm). Optionally, the composition can be coated as a stripe over the length of the substrate strip. The substrate may also have an adhesive on the surface opposite that on which the indicator composition is disposed. In this way, the indicator may be used as a tape or label for attachment to the article to be sterilized.

The hydrogen peroxide vapor sterilization procedure used is conventional, and is disclosed in, for example, U.S. Pat. Nos. 4,756,882, 4,643,876, 4,956,145, and 5,445,792. Preferably, it is a plasma-based sterilization system.

In general, the article to be sterilized is placed in a sterilization chamber with any of the preferred embodiments of hydrogen peroxide indicator of the invention, and a dose of hydrogen peroxide, which generally comes pre-measured, is delivered to the chamber. Vapor is generated and allowed to fill the container for an appropriate length of time after which the sterilization is complete. The indicator is then inspected for color change. The equipment and the entire procedure generally are controlled electronically. When sterilizing medical instruments, one cycle is often sufficient. The medical instruments are often packaged, with the entire package being placed into the sterilizing compartment. The package allows the hydrogen peroxide to penetrate and effect sterilization of the instruments, while subsequently protecting the instruments from contamination in air. The temperatures used in the process of the present invention are all generally less than 65° C.

The peracetic acid sterilization procedures that may be used are conventional, and are disclosed in, for example, U.S. Pat. Nos. 6,287,518 and 4,892,706. A conventional liquid peracetic acid sterilization procedure is disclosed in U.S. Pat. No. 4,892,706.

In general, the article to be sterilized is placed in a sterilization chamber with any of the preferred embodiments of peracetic acid indicator of the invention. Concentrated peracetic acid is then diluted in a buffer solution to form a sterilant solution, which is introduced to and circulated throughout the sterilization chamber. The article to be sterilized and the indicator are exposed to the sterilant solution for at least approximately 12 minutes at a temperature at or below about 60° C. The sterilization chamber is then drained and rinsed with water. The rinsed article and indicator are removed from the sterilization chamber and the indicator is inspected for color change.

The invention will be illustrated in greater detail by the following specific examples. It is understood that these examples are given by way of illustration and are not meant to limit the disclosure or the claims to follow. All percentages in the examples, and elsewhere in the specification, are by weight unless otherwise specified.

EXAMPLES

Control Example A without Metal Salts

Control indicator compositions (Control Indicator Composition A) were prepared by shaking 10 milliliters (ml) of a binder-solution containing 7 wt-% percent of hydroxypropyl cellulose in 9 parts methanol: 1 part water, with approximately 0.1 gram (g) or a sufficient amount of colorant (0.1 wt-% to 5 wt-%) to give a good color in a glass vial. The colorants used to prepare these control indicator compositions are listed in Table 1a.

Example 1

Preparation of Indicator Compositions

Indicator compositions (Indicator Composition 1) listed in Table 1b were prepared by adding 1 drop of a saturated cupric chloride water solution to the control indicator compositions described in Control Example A and shaking in the glass vial.

Coating of Indicator Compositions

Indicator compositions and control indicator compositions were coated on plastic polystyrene backing (commercially available from Plastic Suppliers Inc., Chicago Heights, Ill.) using a number 16 Meyer bar (commercially available from R. D. Specialties, Webster, N.Y.). The coated inks were dried at 50° C. in an oven (commercially available as "Despatch Style V 29" from Despatch Oven Co., Minneapolis, Minn.) for 2 minutes. The coated films were cut using scissors to obtain indicators approximately 2 centimeters (cm) by 13 cm.

Test Method

Each coated indicator composition and coated control indicator composition was placed on an instrument tray lid and exposed to a full Hospital 100 cycle of a hydrogen peroxide plasma sterilization procedure at 45-55° C. in a STERRAD 100SI GMP Sterilizer, obtained from Advanced Sterilization Products Co., Irvine, Calif. During the sterilization procedure a vacuum was drawn in the sterilization chamber for 5-6 minutes until the pressure was reduced to 40.0 Pa. A 1.8 ml aliquot of an aqueous solution of 58-60 percent hydrogen peroxide was then injected into the empty sterilization chamber, yielding an empty chamber concentration of 6-7 mg/l hydrogen peroxide. Hydrogen peroxide vapor was allowed to diffuse throughout the chamber for 44 minutes at $8 \times 10^2$ to $13.3 \times 10^2$ Pa. A vacuum was then drawn, reducing the pressure to 66.7 Pa and removing all detectable hydrogen peroxide vapor from the chamber. A plasma phase was then generated in the chamber by emitting an RF power source at 400 watts and 13.56 MegaHertz (MHz) for about 15-16 minutes at 66.7 Pa, after which the chamber was vented for 3-4 minutes until atmospheric pressure was reached in the chamber. After exposure to the sterilization procedure the indicators were removed from the tray lid and examined for color change. The results for each control indicator composition and indicator composition are described in Table 1a and Table 1b, respectively.

After the colorants were exposed to a full Hospital 100 cycle of hydrogen peroxide plasma sterilization procedure as described above, most of the control indicator compositions (Table 1a) did not change from their initial color. However, Victoria green S extra became colorless; Basic blue 41, Toluidine blue O, and Arsenazo 111 became lighter; Quinaldine red and Alkali blue 4B became slightly lighter; and Violamine R changed from a light pink to pink/violet (darker).

After cupric chloride was added to the indicator composition, most of the colorants either became colorless or significantly lighter when exposed to hydrogen peroxide plasma as described above (Table 1b). The colorants including cupric chloride that did not change or changed so slightly as to make the change difficult to see with the human eye were Cibacron brilliant red 3B, Amaranth, and Brilliant black BN; Nile blue A changed from light blue to light gray; Bordeaux R changed from light pink to a slightly lighter pink; Direct red 75 changed from almost colorless to colorless; and Ponceau SS changed from pink/beige to light purple/pink.

As demonstrated in Example 2, below (Table 2), the choice of metal ion can affect the color change. For instance an indicator composition including one metal ion can produce a color change in an indicator composition exposed to a sterilant that is different from that of an indicator composition including the same colorant with a different metal ion that is also exposed to a sterilant. Compare, for example, the colorant Chromotrope 2B listed in Table 2, No. 7 (with ferrous chloride) that turns colorless with Chromotrope 2B listed in Table 1b, No. 57 (with cupric chloride) that turns beige.

Example 2

Preparations of Indicator Compositions Using Ferrous Chloride

Indicator compositions (Indicator Composition 2, Table 2) were prepared by adding 1 drop of a saturated ferrous chloride water solution to the control indicator compositions described in Control Example A and shaking in the glass vial. The colorants used with the ferrous chloride are listed in Table 2.

Indicator compositions and control indicator compositions were coated on plastic backings and sterilized as described in Example 1.

The results for each control indicator composition (Control Indicator Composition A) and Indicator Composition 2 are shown in Table 1a and Table 2, respectively.

After the addition of ferrous chloride to the control composition, each of the colorants listed in Table 2 either became colorless or significantly lighter when exposed to hydrogen peroxide plasma as described above.

Control Example B without Metal Salts

Control indicator compositions (Control Indicator B, Table 3a) were prepared by shaking 10 milliliters (ml) of a binder solution containing 5 wt-% of hydroxypropyl cellulose in 6 parts methanol: 4 parts water, with approximately 0.1 g or a sufficient amount of colorant (0.1 wt-% to 5 wt-%) to give a good color in a glass vial. The colorants used in the Control Indicator Composition B for Examples 3-10 are listed in Table 3a.

Example 3

Preparation of Indicator Compositions Using Cobalt Chloride

A drop of cobalt chloride salt solution containing 1 g of salt to 3.25 g of water was added to the control indicator composition described in Control Example B and shaken in a glass vial. The colorants used with cobalt chloride are listed in Table 3b.

Indicator compositions and control indicator compositions were coated on plastic backings and sterilized as described in Example 1.

The results for each Control Indicator Composition B and Indicator Composition 3 are shown in Table 3a and Table 3b respectively.

After the colorants were exposed to a full Hospital 100 cycle of hydrogen peroxide plasma sterilization procedure as described above, most of the colorants did not change from their initial color. However, Guinea green B became almost colorless; Acid fuchsin sodium salt became lighter; Nile blue A, Arsenazo 1, Basic red 14, Basic red 15, and Alkali blue 4B became slightly lighter; Azure B became significantly lighter, Aniline blue changed from blue to gray/green; Quinaldine red changed from muddy pink to light pink, and Acid blue 92 changed from lilac to light violet.

After the addition of cobalt chloride to the control composition, all of the colorants listed in Table 3b became colorless when exposed to hydrogen peroxide plasma as described above.

Example 4

Preparation of Indicator Compositions Using Cobalt Acetate

Indicator compositions were prepared as described in Example 3 except a drop of cobalt acetate salt solution containing 1 g of salt to 3.25 g of water was added to the initial composition and shaken in a glass vial. The colorants used are listed in Table 4

Indicator compositions and control indicator compositions were coated on plastic backings and sterilized as described in Example 1.

The results for each control indicator composition and Indicator Composition 4 are shown in Table 3a and Table 4, respectively.

After the addition of cobalt acetate to the control composition each of the colorants listed in Table 4 became colorless when exposed to hydrogen peroxide plasma as described above.

Example 5

Preparation of Indicator Compositions Using Cupric Chloride

Indicator compositions were prepared as described in Example 3 except four drops of cupric chloride salt solution containing 1 g of salt to 13 g of water was added to the initial composition and shaken in a glass vial. The colorants used are listed in Table 5

Indicator compositions and control indicator compositions were coated on plastic backings and sterilized as described in Example 1.

The results for each control indicator composition and Indicator Composition 5 are shown in Table 3a and Table 5, respectively.

After the addition of cupric chloride to the control composition, each of the colorants listed in Table 5 became colorless when exposed to hydrogen peroxide plasma as described above.

Example 6

Preparation of Indicator Compositions Using Cupric Sulfate

Indicator compositions were prepared as described in Example 3 except four drops of cupric sulfate salt solution containing 1 g of salt to 13 g of water was added to the initial composition and shaken in a glass vial. The colorants used are listed in Table 6

Indicator compositions and control indicator compositions were coated on plastic backings and sterilized as described in Example 1.

The results for each control indicator composition and Indicator Composition 6 are shown in Table 3a and Table 6, respectively.

The addition of cupric sulfate to the control composition of the colorants listed in Table 6 did not show as dramatic results as the preceding examples. Each colorant changed color when exposed to hydrogen peroxide plasma as described above; however, Azure B became clear, Methylene violet 3RAX became almost colorless, and Basic red 15 became significantly lighter. Patent blue violet changed from green/blue to green/gray; Guinea green B and Fast green FCF changed from green to a mottled green on clear when exposed to hydrogen peroxide plasma.

Example 7

Preparation of Indicator Compositions Using Ferrous Chloride

Indicator compositions were prepared as described in Example 3 except a drop of ferrous chloride salt solution containing 1 g of salt to 3.25 g of water was added to the initial composition and shaken in a glass vial. The colorants used are listed in Table 7.

Indicator compositions and control indicator compositions were coated on plastic backings and sterilized as described in Example 1.

The results for each control indicator composition and Indicator Composition 7 are shown in Table 3a and Table 7, respectively.

After the addition of ferrous chloride to the control composition, the colorants listed in Table 7 became colorless when exposed to hydrogen peroxide plasma as described above.

Example 8

Preparation of Indicator Compositions Using Ferrous Sulfate

Indicator compositions were prepared as described in Example 3 except four drops of ferrous sulfate salt solution containing 1 g of salt to 13 g of water was added to the initial composition and shaken in a glass vial. The colorants used are listed in Table 8

Indicator compositions and control indicator compositions were coated on plastic backings and sterilized as described in Example 1.

The results for each control indicator composition and Indicator Composition 8 are shown in Table 3a and Table 8, respectively.

After the addition of ferrous sulfate to the control composition, each of the colorants either became colorless, almost colorless, or significantly lighter when exposed to hydrogen peroxide plasma as described above.

Example 9

Preparation of Indicator Compositions Using Chromium Potassium Sulfate

Indicator compositions were prepared as described in Example 3 except a drop of chromium potassium sulfate salt solution containing 1 g of salt to 3.25 g of water was added to the initial composition and shaken in a glass vial. The colorants used are listed in Table 9. Indicator compositions and control indicator compositions were coated on plastic backings and sterilized as described in Example The results for each control indicator composition and Indicator Composition 9 are shown in Table 3a and Table 9, respectively.

After the addition of chromium potassium sulfate to the control composition, each of the colorants except Congo red became colorless when exposed to hydrogen peroxide plasma as described above. Congo red changed from red to brown, which is a significant change to be seen by the human eye.

Example 10

Preparation of Indicator Compositions Using Cupric Acetate

Indicator compositions were prepared as described in Example 3 except a drop of cupric acetate salt solution containing 1 g of salt to 3.25 g of water was added to the initial composition and shaken in a glass vial. The colorants used are listed in Table 10.

Indicator compositions and control indicator compositions were coated on plastic backings and sterilized as described in Example 1.

The results for each control indicator composition B and Indicator Composition 10 are shown in Table 3a and Table 10, respectively.

After the addition of cupric acetate to the control composition, the colorants listed in Table 10 became almost colorless, significantly lighter, or lighter except Xylidine ponceau 2R when exposed to hydrogen peroxide plasma as described above. Xylidine ponceau 2R did not change color with the addition of cupric acetate and exposure to hydrogen peroxide plasma.

Example 11

Preparation of Indicator Compositions with Cupric Acetate and Device

Indicator compositions were prepared by dissolving 0.3 g of colorant in 90 ml of water. The colorants are listed in Table 11. The resulting solution was divided equally into 3 boats. A control indicator was made by immersing an 11 cm circle of Whatman Grade 1 filter paper in the solution, allowing the excess solution to drip from the paper, and drying for approximately 1 hour. The color of the dried control is recorded in Table 11.

A second solution (Indicator Composition 11) was prepared by adding 1.0 g of a cupric acetate $\{Cu(C_2H_3O_2)_2 \cdot H_2O\}$ (available from Mallinckrodt, Inc., Hazelwood, Mo.) to 13 ml of water.

Five ml of the second solution was added to the solution in each boat. Three more 11 cm circles of filter paper were immersed one in each boat, allowed to drip and dried like the control. The color of the dried colorant and metallic salt composition is recorded in Table 11.

Adhesive (3M VHB acrylate adhesive on a release liner) was applied by transfer of the adhesive from the release liner to one side of each dried filter paper. A 1.9 cm (0.75 inch) circle was cut from the adhesive backed filter paper. The smaller adhesive circle was applied to the center of a 5.08 cm square (2 inch) by 0.25 millimeter (0.01 inch) thick piece of TYVEK type 10 1025 D spunbond olefin backing, available from E. I. du Pont de Nemours and Company, Wilmington, Del. The circle was enclosed within a device in the following manner. A 5.08 cm (2 inch) square by 0.25 mm (0.01 inch) thick piece of polyvinyl chloride (available as PJN-9708623 from Perfecseal, Minneapolis, Minn.) having a central 2.54 cm (1 inch) square by 0.95 cm (⅜ inch) deep vapor head space was glued using, Loctite 411 instant adhesive, to the spunbond backing Test Method The devices were processed in the STERIS SYSTEM 1 sterilizer, obtained from STERIS Corporation, Mentor, Ohio. The devices were sealed in the sterilizer and exposed to a preliminary wash with an anticorrosive buffer solution. Sixty (60) ml of 35 percent liquid peracetic acid was then introduced to the buffer solution and circulated throughout the sterilization chamber for 12 minutes at 50-56° C. The circulating sterilant had a liquid peracetic acid concentration of 0.2 percent and a pH of 6.4. The sterilant was then drained and the sterilizing chamber was washed with water four times. The devices were removed and examined visually for color changes. The results are recorded in Table 11. Some of the devices changed color on the edges of the circle, but retained the initial color in the center. New indicator devices were tested without applying an adhesive coating to the back of the colored filter paper. The results of Examples 11-13 are noted in Tables 11, 12, and 13.

Example 12

Preparation of Indicator Compositions with Copper Sulfate and Devices

Indicator compositions were prepared as for Example 11. The colorants used are listed in Table 12. The second solution (Indicator Composition 12) was prepared by adding 1.0 g of copper sulfate ($CuSO_4.5H_2O$) (available from Mallinckrodt, Inc., Hazelwood, Mo.) to 13 ml of water. Devices were prepared and tested as described in Example 11. The results are recorded in Table 12.

Example 13

Preparation of Indicator Compositions with Cobalt Acetate and Devices

Indicator compositions were prepared as for Example 11. The colorants used are listed in Table 13. The second solution (Indicator Composition 13) was prepared by adding 1.0 g of cobalt(II) acetate tetrahydrate $\{Co(C_2H_3O_2)_2.4H_2O\}$ (available from Sigma-Aldrich Fine Chemicals, St. Louis, Mo.) to 13 ml of water. Devices were prepared and tested as described in Example 11. The results are recorded in Table 13.

TABLE 1a

Control Indicator Composition A Colorants and Results after Sterilization

| No. | Colorant | Colorant Class | Color Index Number | Initial Color without Metallic Salts | Color Change in Sterilizer |
|---|---|---|---|---|---|
| 1 | [1]Alphazurine A | Methane | 42080 | Blue/green | None |
| 2 | [1]Azocarmine G | Diazine | 50085 | Purple/pink | None |
| 3 | Victoria green S extra | Not known | Not known | Green | Colorless |
| 4 | [1]Methyl violet 2B (Basic violet 1) | Methane | 42535 | Purple | None |
| 5 | [1]Ethyl violet (Basic violet 4) | Methane | 42600 | Blue | None |
| 6 | [1]Alizarin violet 3R | Anthraquinone | 61710 | Light lilac | None |
| 7 | [1]Basic blue 41 | Not known | Not known | Dark lilac | Lighter |
| 8 | [4]FD/C blue 1 | Methane | 42090 | Light blue | None |
| 9 | [1]Toluidine blue O (Basic blue 17 or Tolonium chloride) | Thiazine | 52040 | Violet | Lighter |
| 10 | [1]Nile blue A | Oxazine | 51180 | Purple/blue | None |
| 11 | [1]Quinaldine red | Cyanine | None | Red/gray | Slightly lighter |
| 12 | [1]Basic blue 3 | Oxazine | 51004 | Blue/green | None |
| 13 | [1]Acid black 24 | Diazo | 26370 | Blue/black | None |
| 14 | [1]Acid red 97 | Diazo | 22890 | Orange | None |
| 15 | [1]Cibacron brilliant red 3B | Monoazo | Not known | Pale pink | None |
| 16 | [1]Sulforhodamine B | Xanthene | 45100 | Hot pink | None |
| 17 | [1]Direct blue 71 | Triazo | 34140 | Purple/black | None |
| 18 | [1]Chromotrope 2B | Monoazo | 16575 | Pink-beige | None |
| 19 | [1]Brilliant blue R (Acid blue 83 or Coomassie brilliant blue R) | Methane | 42660 | Blue | None |
| 20 | [1]Amaranth | Monoazo | 16185 | Pink/gray | None |
| 21 | [1]Rhodanine 6G | Xanthene | 45160 | Hot pink | None |
| 22 | [5]Brilliant cresyl blue BB | Oxazine | 51010 | Blue | None |
| 23 | [3]D & C red No. 33 | Monoazo | 17200 | Red | lilac |
| 24 | [1]Bordeaux R | Monoazo | 16180 | Light pink | None |
| 25 | [1]Direct red 75 | Diazo | 25380 | Pale pink | None |
| 26 | [1]Acid violet 7 | Monoazo | 18055 | Lilac | None |
| 27 | [1]Acid violet 5 | Monoazo | 18125 | Dark pink | None |
| 28 | [1]Plasmocorinth B | Monoazo | 16680 | Dark pink | None |
| 29 | [1]Brilliant crocein MOO | Diazo | 27290 | Orange | None |
| 30 | [1]Methylene green | Thiazine | 52020 | Pale blue/gray | Pale pink/gray |
| 31 | [1]Methylene violet 3RAX | Diazine | 50206 | Pink | None |
| 32 | [1]Ponceau SS | Diazo | 27190 | Pink/beige | None |
| 33 | [1]Reactive black 5 | Diazo | 20505 | Blue/black | None |
| 34 | [2]Basic red 15 | Not known | Not known | Hot pink | None |
| 35 | [3]Acid green AX986 | Not known | Not known | Lime green | None |
| 36 | [1]Lissamine green B (Acid Green 50 or Wool Green S) | Methane | 44090 | Blue/green | None |
| 37 | [1]Erioglaucine | Methane | 42090 | Blue/green | None |
| 38 | [1]Violamine R | Xanthene | 45190 | Light pink | Pink/violet |
| 39 | [1]Brilliant black BN | Diazo | 28440 | Dark gray | None |
| 40 | [1]Arsenazo 111 | Diazo | None | Dark lilac | Lighter |
| 41 | [3]Alkali blue 4B | Methane | 42750 | Blue | Slightly lighter |
| 42 | [3]Coomassie violet R 150 | Methane | 42650 | Grey/blue | None |

TABLE 1a-continued

Control Indicator Composition A Colorants and Results after Sterilization

| No. | Colorant | Colorant Class | Color Index Number | Initial Color without Metallic Salts | Color Change in Sterilizer |
|---|---|---|---|---|---|
| 43 | [1]Acid blue 92 | Monoazo | 13390 | Lilac | Light violet |
| 44 | [1]Acid blue 29 | Diazo | 20460 | Grey/blue | None |
| 45 | [1]Xylidine ponceau 2R | Monoazo | 16150 | Orange | None |
| 46 | [1]Reactive blue 2 | Anthraquinone | 61211 | Blue/gray | None |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Warner-Jenkinson, St. Louis, MO.
[5]Commercially available from Kodak, Rochester, NY

TABLE 1b

Indicator Composition 1 Colorants and Results after Sterilization

| No. | Colorant | Colorant Class | Color Index Number | Initial Color | Color with Cupric Chloride | Color Change in Sterilizer |
|---|---|---|---|---|---|---|
| 1 | [1]Alphazurine A | Methane | 42080 | Blue/green | Blue/green | Almost colorless |
| 2 | [1]Azocarmine G | Diazine | 50085 | Purple/pink | Purple/pink | Significantly lighter |
| 3 | Victoria green S extra | Not known | Not known | Green | Green | Colorless |
| 4 | [1]Methyl violet 2B (Basic violet 1) | Methane | 42535 | Purple | Purple | Colorless |
| 5 | [1]Ethyl violet (Basic violet 4) | Methane | 42600 | Blue | Blue | Colorless |
| 6 | [1]Alizarin violet 3R | Anthraquinone | 61710 | Light lilac | Light lilac | Lighter |
| 7 | [1]Basic blue 41 | Not known | Not known | Dark lilac | Dark lilac | Colorless |
| 8 | [4]FD/C blue 1 | Methane | 42090 | Light blue | Light blue | Almost colorless |
| 9 | [1]Toluidine blue O (Basic blue 17 or Tolonium chloride) | Thiazine | 52040 | Violet | Blue/gray | Colorless |
| 10 | [1]Nile blue A | Oxazine | 51180 | Purple/blue | Very Light blue, Almost Colorless | Light gray |
| 11 | [1]Quinaldine red | Cyanine | None | Red/gray | Pale pink/gray | Colorless |
| 12 | [1]Basic blue 3 | Oxazine | 51004 | Blue/green | Blue | Colorless |
| 13 | [1]Acid black 24 | Diazo | 26370 | Blue/black | Blue/black | Colorless |
| 14 | [1]Acid red 97 | Diazo | 22890 | Orange | Orange | Colorless |
| 15 | [1]Cibacron brilliant red 3B | Monoazo | Not known | Pale pink | Pale pink | No change |
| 16 | [1]Sulforhodamine B | Xanthene | 45100 | Hot pink | Hot pink | Very light pink |
| 17 | [1]Direct blue 71 | Triazo | 34140 | Purple/black | Purple/black | Slightly lighter |
| 18 | [1]Chromotrope 2B | Monoazo | 16575 | Pink-beige | Dark gray | Beige |
| 19 | [1]Brilliant blue R (Acid blue 83 or Coomassie brilliant blue R) | Methane | 42660 | Blue | Blue | Colorless |
| 20 | [1]Amaranth | Monoazo | 16185 | Pink/gray | Pink/gray | No change |
| 21 | [1]Rhodanine 6G | Xanthene | 45160 | Hot pink | Hot pink | Almost colorless |
| 22 | [5]Brilliant cresyl blue BB | Oxazine | 51010 | Blue | Blue | Colorless |
| 23 | [3]D & C red No. 33 | Monoazo | 17200 | Red | Purple/pink | Tan |
| 24 | [1]Bordeaux R | Monoazo | 16180 | Light pink | Light pink | Slightly lighter |
| 25 | [1]Direct red 75 | Diazo | 25380 | Pale pink | Almost colorless | Colorless |
| 26 | [1]Acid violet 7 | Monoazo | 18055 | Lilac | Lilac | Very light lilac |
| 27 | [1]Acid violet 5 | Monoazo | 18125 | Dark pink | Light red | Colorless |
| 28 | [1]Plasmocorinth B | Monoazo | 16680 | Dark pink | Light violet | Colorless |
| 29 | [1]Brilliant crocein MOO | Diazo | 27290 | Orange | Light red | Very pale orange |
| 30 | [1]Methylene green | Thiazine | 52020 | Pale blue/gray | Pale blue/gray | Colorless |
| 31 | [1]Methylene violet 3RAX | Diazine | 50206 | Pink | Pink | Colorless |
| 32 | [1]Ponceau SS | Diazo | 27910 | Pink/beige | Pink/beige | Light purple/pink |
| 33 | [1]Reactive black 5 | Diazo | 20505 | Blue/black | Blue/black | Beige |
| 34 | [3]Basic red 15 | Not known | Not known | Hot pink | Hot pink | Colorless |
| 35 | [2]Acid green AX986 | Not known | Not known | Lime green | Lime green | Tan |
| 36 | [1]Lissamine green B (Acid Green 50 or Wool Green S) | Methane | 44090 | Blue/green | Blue/green | Colorless |

TABLE 1b-continued

Indicator Composition 1 Colorants and Results after Sterilization

| No. | Colorant | Colorant Class | Color Index Number | Initial Color | Color with Cupric Chloride | Color Change in Sterilizer |
|---|---|---|---|---|---|---|
| 37 | [1]Erioglaucine | Methane | 42090 | Blue/green | Blue/green | Colorless |
| 38 | [1]Violamine R | Xanthene | 45190 | Light pink | Pink/violet | Very light pink |
| 39 | [1]Brilliant black BN | Diazo | 28440 | Dark gray | Dark gray | No change |
| 40 | [1]Arsenazo 111 | Diazo | None | Dark lilac | Blue/black | Almost colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Warner-Jenkinson, St. Louis, MO.
[5]Commercially available from Kodak, Rochester, NY.

TABLE 2

Indicator Composition 2 Colorants and Results after Sterilization

| No. | Colorant | Colorant Class | Color Index Number | Initial Color | Color with Ferrous Chloride | Color Change in Sterilizer |
|---|---|---|---|---|---|---|
| 1 | [1]Alphazurine A | Methane | 42080 | Blue/green | Blue/green | Colorless |
| 2 | [1]Azocarmine G | Diazine | 50085 | Purple/pink | Purple/pink | Colorless |
| 3 | Victoria green S extra | Not known | Not known | Green | Green | Colorless |
| 4 | [1]Methyl violet 2B (Basic violet 1) | Methane | 42535 | Purple | Purple | Colorless |
| 5 | [1]Ethyl violet (Basic violet 4) | Methane | 42600 | Blue | Blue | Colorless |
| 6 | [1]Alizarin violet 3R | Anthraquinone | 61710 | Light lilac | Light lilac | Colorless |
| 7 | [1]Basic blue 41 | Not known | Not known | Dark lilac | Dark lilac | Colorless |
| 8 | [4]FD/C blue 1 | Methane | 42090 | Light blue | Light blue | Colorless |
| 9 | [1]Toluidine blue O | Thiazine | 52040 | Violet | Blue/gray | Colorless |
| 10 | [1]Nile blue A | Oxazine | 51180 | Purple/blue | Blue/green | Colorless |
| 11 | [1]Quinaldine red | Cyanine | None | Red/gray | Pink/gray | Colorless |
| 12 | [1]Basic blue 3 | Oxazine | 51004 | Blue/green | Blue/green | Colorless |
| 13 | [1]Acid black 24 | Diazo | 26370 | Blue/black | Blue/black | Colorless |
| 14 | [1]Acid red 97 | Diazo | 22890 | Orange | Orange | Colorless |
| 15 | [1]Cibacron brilliant red 3B | Monoazo | Not known | Pale pink | Pale pink | Colorless |
| 16 | [1]Sulforhodamine B | Xanthene | 45100 | Hot pink | Hot pink | Colorless |
| 17 | [1]Direct blue 71 | Triazo | 34140 | Purple/black | Purple/black | Significantly lighter |
| 18 | [1]Chromotrope 2B | Monoazo | 16575 | Pink-beige | Pink-beige | Colorless |
| 19 | [1]Brilliant blue R (Acid blue 83 or Coomassie brilliant blue R) | Methane | 42660 | Blue | Blue | Colorless |
| 20 | [1]Amaranth | Monoazo | 16185 | Pink/gray | Pink/gray | Significantly lighter |
| 21 | [1]Rhodanine 6G | Xanthene | 45160 | Hot pink | Hot pink | Colorless |
| 22 | [5]Brilliant cresyl blue BB | Oxazine | 51010 | Blue | Blue | Colorless |
| 23 | [3]D & C red No. 33 | Monoazo | 17200 | Red | Red | Colorless |
| 24 | [1]Bordeaux R | Monoazo | 16180 | Light pink | Light pink | Significantly lighter |
| 25 | [1]Direct red 75 | Diazo | 25380 | Pale pink | Pale pink | Colorless |
| 26 | [1]Acid violet 7 | Monoazo | 18055 | Lilac | Lilac | Colorless |
| 27 | [1]Acid violet 5 | Monoazo | 18125 | Dark pink | Dark pink | Colorless |
| 28 | [1]Plasmocorinth B | Monoazo | 16680 | Dark pink | Brown | Colorless |
| 29 | [1]Brilliant crocein MOO | Diazo | 27290 | Orange | Orange | Colorless |
| 30 | [1]Methylene green | Thiazine | 52020 | Pale blue/gray | Pale blue/gray | Colorless |
| 31 | [1]Methylene violet 3RAX | Diazine | 50206 | Pink | Pink | Colorless |
| 32 | [1]Ponceau SS | Diazo | 27190 | Pink/beige | Pink/beige | Colorless |
| 33 | [1]Reactive black 5 | Diazo | 20505 | Blue/black | Blue/black | Colorless |
| 34 | [2]Basic red 15 | Not known | Not known | Hot pink | Hot pink | Colorless |
| 35 | [3]Acid green AX986 | Not known | Not known | Lime green | Lime green | Colorless |
| 36 | [1]Lissamine green B (Acid Green 50 or Wool Green S) | Methane | 44090 | Blue/green | Blue/green | Colorless |
| 37 | [1]Erioglaucine | Methane | 42090 | Blue/green | Blue/green | Colorless |

TABLE 2-continued

Indicator Composition 2 Colorants and Results after Sterilization

| No. | Colorant | Colorant Class | Color Index Number | Initial Color | Color with Ferrous Chloride | Color Change in Sterilizer |
|---|---|---|---|---|---|---|
| 38 | [1]Violamine R | Xanthene | 45190 | Light pink | Pink/Violet | Colorless |
| 39 | [1]Brilliant black BN | Diazo | 28440 | Dark gray | Dark gray | Colorless |
| 40 | [1]Arsenazo 111 | Diazo | None | Dark lilac | Dark gray | Colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Warner-Jenkinson, St. Louis, MO.
[5]Commercially available from Kodak, Rochester, NY TABLE 3a Control Indicator B Colorants and Results after Sterilization

| No. | Colorant | Colorant Class | Color Index Number | Initial Color without Metallic Salts | Color Change in Sterilizer |
|---|---|---|---|---|---|
| 1 | [1]Azocarmine G | Diazine | 50085 | Purple/pink | None |
| 2 | [1]Ethyl violet (Basic violet 4) | Methane | 42600 | Dark purple/blue | None |
| 3 | [1]Victoria pure blue BO (Basic blue 7) | Methane | 42595 | Blue | None |
| 4 | [1]Nile blue A | Oxazine | 51180 | Lilac | Slightly lighter |
| 5 | [1]Quinaldine red | Cyanine | None | Muddy pink | Light pink |
| 6 | [3]Patent blue violet | Methane | None | Green/blue | None |
| 7 | [1]Acid fuchsin sodium salt | Methane | 42685 | Hot pink | Lighter |
| 8 | [1]Eriochrome black T | Monoazo | 14645 | Light muddy pink | None |
| 9 | [1]Eriochrome blue black B | Monoazo | 14640 | Muddy pink | None |
| 10 | [1]Aniline blue | Methane | 42780 | Blue | Gray/green |
| 11 | [1]Azure B | Thiazine | 52010 | Blue | Significantly lighter |
| 12 | [1]Guinea green B (Acid green 3) | Methane | 42085 | Green | Almost colorless |
| 13 | [4]D & C green No. 5 | Anthraquinone | Not known | Pale green | None |
| 14 | [4]Keystone soap fluoro green | Not known | Not known | Light green | None |
| 15 | [1]Congo red | Diazo | 22120 | Red | None |
| 16 | [1]Acid blue 113 | Diazo | 26360 | Blue/gray | None |
| 17 | [1]Acid red 151 | Diazo | 26900 | Pink | None |
| 18 | [1]Arsenazo 1 | Monoazo | None | Light pink | Slightly lighter |
| 19 | [1]Methylene violet 3RAX | Diazine | 50206 | Pink | None |
| 20 | [1]Mordant brown 48 | Monoazo | 11300 | Very light orange | None |
| 21 | [2]Basic red 14 | Not known | Not known | Pink | Slightly lighter |
| 22 | [2]Basic red 15 | Not known | Not known | Pink | Slightly lighter |
| 23 | [1]Fast green FCF | Methane | 42053 | Green | None |
| 24 | [1]Erioglaucine | Methane | 42090 | Green/blue | None |
| 25 | [3]Alkali blue 4B | Methane | 42750 | Blue | Slightly lighter |
| 26 | [3]Coomassie violet R 150 | Methane | 42650 | Grey/blue | None |
| 27 | [1]Acid blue 92 | Monoazo | 13390 | Lilac | Light violet |
| 28 | [1]Acid blue 29 | Diazo | 20460 | Grey/blue | None |
| 29 | [1]Xylidine ponceau 2R | Monoazo | 16150 | Orange | None |
| 30 | [1]Reactive blue 2 | Anthraquinone | 61211 | Blue/gray | None |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Keystone Aniline Corp., Chicago, IL.

TABLE 3b

Indicator Composition 3 Colorants and Results after Sterilization

| No. | Colorant | Colorant Class | Color Index Number | Initial Color | Color with Cobalt Chloride | Color Change in Sterilizer |
|---|---|---|---|---|---|---|
| 1 | [3]Patent blue violet | Methane | None | Green/blue | Green/blue | Colorless |
| 2 | [1]Aniline blue | Methane | 42780 | Blue | Blue | Colorless |
| 3 | [1]Congo red | Diazo | 22120 | Dark orange | Dark orange | Colorless |
| 4 | [1]Arsenazo 1 | Monoazo | None | Light Pink | Grey | Colorless |
| 5 | [1]Acid blue 92 | Monoazo | 13390 | Lilac | Lilac | Colorless |
| 6 | [1]Acid blue 29 | Diazo | 20460 | Gray/blue | Gray/blue | Colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.

TABLE 4

Indicator Composition 4 Colorants and Results after Sterilization

| No. | Colorant | Colorant Class | Color Index Number | Initial Color | Color with Cobalt Acetate | Color Change in Sterilizer |
|---|---|---|---|---|---|---|
| 1 | [1]Nile blue A | Oxazine | 51180 | Lilac | Lilac | Colorless |
| 2 | [1]Eriochrome blue black B | Monoazo | 14640 | Muddy pink | Light violet | Colorless |
| 3 | [4]D & C green No. 5 | Anthraquinone | Not known | Light green | Light green | Colorless |
| 4 | [2]Basic red 15 | Not known | Not known | Pink | Pink | Colorless |
| 5 | [1]Erioglaucine | Methane | 42090 | Green/blue | Green/blue | Colorless |
| 6 | [1]Reactive blue 2 | Anthraquinone | 61211 | Blue/gray | Blue/gray | Colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Keystone Aniline Corp., Chicago, IL.

TABLE 5

Indicator Compositios 5 Colorants and Results after Sterilization

| No. | Colorant | Colorant Class | Color Index Number | Initial Color | Color with Cupric Chloride | Color Change in Sterilizer |
|---|---|---|---|---|---|---|
| 1 | [1]Azocarmine G | Diazine | 50085 | Rose | Light rose | Colorless |
| 2 | [1]Victoria pure blue BO (Basic blue 7) | Methane | 42595 | Blue | Dank blue | Colorless |
| 3 | [1]Acid fuchsin sodium salt | Methane | 42685 | Hot pink | Pink | Colorless |
| 4 | [4]D & C green No. 5 | Anthraquinone | Not known | Pale green | Very pale green | Colorless |
| 5 | [4]Keystone soap fluoro green | Not known | Not known | Light green | Light green | Colorless |
| 6 | [2]Basic red 14 | Not known | Not known | Pink | Pink | Colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Keystone Aniline Corp., Chicago, IL.

TABLE 6

Indicator Composition 6 Colorants and Results after Sterilization

| No. | Colorant | Colorant Class | Color Index Number | Initial Color | Color with Cupric Sulfate | Color Change in Sterilizer |
|---|---|---|---|---|---|---|
| 1 | [2]Patent blue violet | Methane | None | Green/blue | Green/blue | Green/gray |
| 2 | [1]Azure B | Thiazine | 52010 | Blue | Blue | Clear |
| 3 | [1]Guinea green B (Acid green 3) | Methane | 42085 | Green | Green | Mottled green on clear |

TABLE 6-continued

Indicator Composition 6 Colorants and Results after Sterilization

| No. | Colorant | Colorant Class | Color Index Number | Initial Color | Color with Cupric Sulfate | Color Change in Sterilizer |
|---|---|---|---|---|---|---|
| 4 | [1]Methylene violet 3RAX | Diazine | 50206 | Pink | Pink | Almost colorless |
| 5 | [2]Basic red 15 | Not known | Not known | Pink | Pink | Significantly lighter |
| 6 | [1]Fast green FCF | Methane | 42053 | Green | Green | Mottled green on clear |

[1]Commercially available from Sigma-Aldrich Fine Chemicals, St. Louis, MO.
[2]Commercially available from Spectra, Kearny, NJ.

TABLE 7

Indicator Composition 7 Colorants and Results after Sterilization

| No. | Colorant | Colorant Class | Color Index Number | Initial Color | Color with Ferrous Chloride | Color Change in Sterilizer |
|---|---|---|---|---|---|---|
| 1 | [1]Azocarmine G | Diazine | 50085 | Rose | Light rose | Colorless |
| 2 | [1]Victoria pure blue BO (Basic blue 7) | Methane | 42595 | Blue | Dark blue | Colorless |
| 3 | [1]Acid fuchsin sodium salt | Methane | 42685 | Hot pink | Pink | Colorless |
| 4 | [4]D & C green No. 5 | Anthraquinone | Not known | Pale green | Very pale green | Colorless |
| 5 | [4]Keystone soap fluoro green | Not known | Not known | Light green | Light green | Colorless |
| 6 | [2]Basic red 14 | Not known | Not known | Pink | Pink | Colorless |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.
[4]Commercially available from Keystone Aniline Corp., Chicago, IL.

TABLE 8

Indicator Composition 8 Colorants and Results after Sterilization

| No. | Colorant | Colorant Class | Color Index Number | Initial Color | Color with Ferrous Sulfate | Color Change in Sterilizer |
|---|---|---|---|---|---|---|
| 1 | [2]Patent blue violet | Methane | None | Green/blue | Green/blue | Significantly. Lighter |
| 2 | [1]Eriochrome black T | Monoazo | 14645 | Light muddy pink | Light brown | Colorless |
| 3 | [1]Eriochrome blue black B | Monoazo | 14640 | Muddy pink | Pale pink | Colorless |
| 4 | [1]Acid blue 113 | Diazo | 26360 | Blue/gray | Blue/gray | Colorless |
| 5 | [1]Acid red 151 | Diazo | 26900 | Pink | Pink | Almost Colorless |
| 6 | [3]Alkali blue 4B | Methane | 42750 | Blue | Blue | Significantly. lighter |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.

TABLE 9

Indicator Composition 9 Colorants and Results after Sterilization

| No. | Colorant | Colorant Class | Color Index Number | Initial Color | Color with Chromium Potassium Sulfate | Color Change in Sterilizer |
|---|---|---|---|---|---|---|
| 1 | [1]Ethyl violet (Basic violet 4) | Methane | 42600 | Dark purple/blue | Dark purple/blue | Colorless |
| 2 | [1]Quinaldine red | Cyanine | None | Muddy pink | Muddy pink | Colorless |
| 3 | [1]Eriochrome black T | Monoazo | 14645 | Very light muddy pink | Light muddy pink | Colorless |
| 4 | [1]Eriochrome blue black B | Monoazo | 14640 | Muddy pink | Muddy pink | Colorless |

TABLE 9-continued

Indicator Composition 9 Colorants and Results after Sterilization

| No. | Colorant | Colorant Class | Color Index Number | Initial Color | Color with Chromium Potassium Sulfate | Color Change in Sterilizer |
|---|---|---|---|---|---|---|
| 5 | [1]Congo red | Diazo | 22120 | Red | Red | Brown |
| 6 | [1]Acid blue 113 | Diazo | 26360 | Blue/gray | Blue/gray | Colorless |

[1]Commercially available from Sigma-Aldrich Fine Chemicals, St. Louis, MO.

TABLE 10

Indicator Composition 10 Colorants and Results after Sterilization

| No. | Colorant | Colorant Class | Color Index Number | Initial Color | Color with Cupric Acetate | Color Change in Sterilizer |
|---|---|---|---|---|---|---|
| 1 | [1]Acid red 151 | Diazo | 26900 | Pink | Very pale pink, almost clear | Lighter |
| 2 | [1]Mordant brown 48 | Monoazo | 11300 | Very Light Orange | Cream | Lighter |
| 3 | [3]Coomassie violet R 150 | Methane | 42650 | Gray/blue | Purple | Almost colorless |
| 4 | [1]Acid blue 29 | Diazo | 20460 | Purple | Pale purple | Lighter |
| 5 | [1]Xylidine ponceau 2R | Monoazo | 16150 | Orange | Yellow | None |
| 6 | [1]Reactive blue 2 | Anthraquinone | 61211 | Blue/gray | Blue/gray | Slightly lighter |

[1]Commercially available from Sigma-Aldrich Fine Chemicals, St. Louis, MO.
[2]Commercially available from Spectra, Kearny, NJ.
[3]Commercially available from ICN Biomedicals, Costa Mesa, CA.

TABLE 11

Indicator Composition 11 Colorants and Results after Sterilization

| No. | Colorant | Colorant Class | Color Index Number | Initial Color | Color with Cupric Acetate | Color Change in Sterilizer |
|---|---|---|---|---|---|---|
| 1 | Evans blue | Diazo | 23860 | Bright blue | Bright blue | Muddy light purple |
| 2 | Acid violet 7[1] | Monoazo | 18055 | Magenta | Very dark pink | Pale yellow with a slightly pink center |
| 3 | Naphthol blue black | Diazo | 20470 | Navy blue | Dark blue | Dark purple |
| 4 | Reactive black 5[1] | Diazo | 20505 | Blue | Blue | Pink* |
| 5 | Brilliant black BN[1] | Diazo | 28440 | Dark blue | Dark blue | Off-white with light blue center |
| 6 | Brilliant black BN[1] | Diazo | 28440 | Dark blue | Dark blue | Off-white* |
| 7 | Azocarmine B | Diazine | 50090 | Fuchsia | Tan | Yellow with a purple center |
| 8 | Azocarmine B | Diazine | 50090 | Fuchsia | Tan | Yellow* |

*Indicator without adhesive
[1]Commercially available from Sigma-Aldrich Fine Chemicals, St. Louis, MO.

TABLE 12

Indicator Composition 12 Colorants and Results after Sterilization

| No. | Colorant | Colorant Class | Color Index Number | Initial Color | Color with Cobalt Acetate | Color Change in Sterilizer |
|---|---|---|---|---|---|---|
| 1 | Cibacron brilliant red 3B[1] | Monoazo | 18105 | Fuchsia | Fuchsia | Muddy yellow-green with a pink center |
| 2 | Evans blue | Diazo | 23860 | Bright blue | Bright blue | Muddy brown with a slightly blue center |
| 3 | Reactive black 5[1] | Diazo | 20505 | Blue | Blue | Pale blue with white edges |
| 4 | Reactive black 5[1] | Diazo | 20505 | Blue | Blue | Pale spotty blue with white edges* |
| 5 | Brilliant black BN[1] | Diazo | 28440 | Dark blue | Dark blue | Muddy light brown with slightly blue center |

*Indicator without adhesive
[1]Commercially available from Sigma-Aldrich Fine Chemicals, St. Louis, MO.

TABLE 13

Indicator Composition 13 Colorants and Results after Sterilization

| No. | Colorant | Colorant Class | Color Index Number | Initial Color | Color with Cupric Sulfate | Color Change in Sterilizer |
|---|---|---|---|---|---|---|
| 1 | Evans blue | Diazo | 23860 | Bright blue | Bright blue | Dark Blue |
| 2 | Acid violet 7[1] | Monoazo | 18055 | Magenta | Magenta | Pale pink |
| 3 | Acid violet 7[1] | Monoazo | 18055 | Magenta | Magenta | Pale yellow* |
| 4 | Naphthol blue black | Diazo | 20470 | Navy blue | Navy blue | Muddy magenta with tan spots* |
| 5 | Reactive black 5[1] | Diazo | 20505 | Blue | Blue | Dark pink |
| 6 | Brilliant black BN[1] | Diazo | 28440 | Dark blue | Dark blue | Slight lighter blue |
| 7 | Azocarmine B | Diazine | 50090 | Fuchsia | Coral | Purple |

*Indicator without adhesive.
[1]Commercially available from Sigma-Aldrich Fine Chemicals, St. Louis, MO.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of monitoring a sterilization process, the method comprising:
   providing a sterilization indicator comprising a substrate and an indicator composition disposed thereon, the indicator composition comprising:
      at least one salt of a transition metal, selected from the group consisting of cupric chloride, cupric sulfate, cupric acetate, ferrous chloride, ferrous sulfate, cobalt chloride, cobalt acetate, and chromium potassium sulfate;
      at least one colorant that changes color when exposed to hydrogen peroxide in the presence of the at least one salt of a transition metal,
      wherein the at least one colorant is selected from the group consisting of Alphazurine A, Azocarmine G, Victoria green S extra, Methyl violet 2B, Ethyl violet, Basic blue 41, FD/C blue 1, Toluidine blue O, Nile blue A, Quinaldine red, Basic blue 3, Acid black 24, Acid red 97, Sulforhodamine B, Chromotrope 2B, Brilliant blue R, Rhodanine 6G, Brilliant cresyl blue BB, D&C red No. 33, Acid violet 5, Plasmocorinth B, Methylene green, Methylene violet 3RAX, Reactive black 5, Basic red 15, Acid green AX986, Lissamine green B, Erioglaucine, Arsenazo 111, Victoria pure blue BO, Acid fuchsin sodium salt, D & C green No. 5, Basic red 14, Patent blue violet, Azure B, Guinea green B, Fast green FCF, Mordant brown 48, Coomassie violet R 150, Acid blue 29, Alizarin violet 3R, Cibacron brilliant red 3B, Direct blue 71, Direct red 75, Acid violet 7, Brilliant crocein MOO, Ponceau SS, Violamine R, Brilliant Black BN, Eriochrome black T, Eriochrome blue black B, Acid blue 113, Acid red 151, Alkali blue 4B, Aniline blue, Congo red, Arsenazo 1, Acid blue 92, Acid blue 29, D&C green No. 5, Basic red 15, Reactive blue 2, and combinations thereof; and
      at least one binder resin;
   providing an article to be sterilized; and
   exposing the sterilization indicator and the article to be sterilized to a sterilant comprising hydrogen peroxide.

2. The method of claim 1, wherein the at least one colorant is a methane class colorant.

* * * * *